United States Patent [19]
Bevan

[11] Patent Number: 5,792,206
[45] Date of Patent: Aug. 11, 1998

[54] METHODS AND APPARATUS FOR EFFICIENTLY IDENTIFYING IMPLANTABLE CARDIAC DEVICES

[75] Inventor: Gregory Charles Bevan, Canyon Country, Calif.

[73] Assignee: Pacesetter, Inc., Sylmar, Calif.

[21] Appl. No.: 763,023

[22] Filed: Dec. 10, 1996

[51] Int. Cl.$^6$ .................................... A61N 1/37
[52] U.S. Cl. ............................................. 607/32
[58] Field of Search .................. 607/30, 31, 32, 607/9

[56] References Cited

U.S. PATENT DOCUMENTS

| | | | |
|---|---|---|---|
| 4,809,697 | 3/1989 | Causey, III et al. | 607/31 |
| 5,562,713 | 10/1996 | Silvian | 607/32 |

Primary Examiner—Scott M. Getzow

[57] ABSTRACT

Methods and apparatus for identifying implantable cardiac devices are provided. Cardiac devices are classified as belonging to one of various device families, each of which may use a different communications protocol to communicate with an implantable cardiac device programmer. The family identification times anticipated for establishing a communications channel between the programmer and implantable cardiac devices in various device families are stored by the programmer. In addition, the programmer maintains a record of the implantable cardiac device families with which it has successfully communicated. The programmer identifies implantable cardiac devices based on the family identification time and record information, which reduces the amount of time necessary to complete family identification.

12 Claims, 2 Drawing Sheets

METHODS AND APPARATUS FOR EFFICIENTLY IDENTIFYING IMPLANTABLE CARDIAC DEVICES

BACKGROUND OF THE INVENTION

This invention relates to identifying implantable cardiac devices and, more particularly, to identifying which family an implantable cardiac device belongs to.

Implantable cardiac devices, such as pacemakers and cardioverter-defibrillators, typically contain sensing circuitry for monitoring the heartbeat signals produced by a patient's heart. Implantable cardiac devices can determine what type of electrical pulses should be applied to the heart by analyzing these signals. For example, a defibrillation shock can be applied to the heart if an implantable cardioverter-defibrillator determines that the patient is experiencing an episode of fibrillation.

To optimize the operation of an implantable cardiac device, numerous settings may be adjusted by a physician. For example, the physician can adjust the energy levels of the shocks that are used by the device to terminate arrhythmias. The physician can also adjust the frequency and magnitude of the pacing pulses applied to the heart, as well as the threshold conditions that determine when such pacing pulses are to be applied.

Many of these settings are only optimized after the device has been implanted in the patient. To make such adjustments, the physician uses a device known as a programmer. The programmer and implantable cardiac device contain telemetry circuits that support wireless communications. Once a communications channel has been established between the programmer and the implantable cardiac device, the physician can change the settings of the device by entering commands into the programmer and the device can transmit data to the programmer for analysis by the physician.

However, before a communications channel can be established between the programmer and the implantable cardiac device, the programmer must determine what parameters to use in establishing the communications link. Different types of implantable cardiac device use different communications protocols. The programmer must therefore identify the device family for a given implantable cardiac device before communications can be established.

Typically, the process of identifying the family of the implantable cardiac device is one of trial and error. To identify which family a device belongs to, the programmer systematically attempts to establish a communications channel with the device using each possible communications protocol, until the device responds.

Although this technique can be satisfactory in some circumstances, it can be slow, because each attempt to identify the family of the implantable cardiac device can take from 0.5 to 2 seconds to complete. If the physician needs to adjust the settings of the device because, e.g., the patient is in an emergency situation, it is particularly important that the programmer be able to quickly identify the proper family of the implantable cardiac device.

What is therefore needed is a way in which to improve the speed with which a programmer can identify the family of an implantable cardiac device, so that a communications channel between the programmer and the device can be more quickly established.

SUMMARY OF THE INVENTION

In accordance with the principles of the present invention, methods and apparatus are provided for identifying the device family to which an implantable cardiac device belongs. A programmer is preferably provided with a memory that is updated to reflect the types of families of implantable cardiac device with which the programmer regularly communicates. For example, whenever the programmer identifies a device as belonging to a particular family, a histogram stored in the memory can be updated to reflect that a successful identification was made for a device in that family. The histogram is a statistical database that can be used to determine the probability that a given implantable cardiac device will belong to a certain family.

The programmer also stores information in its memory for each device family regarding the time required to establish a communications channel between the programmer and the device and thereby identify the family of the device. This family identification time information is preferably provided to the programmer at the factory or may be updated in the field by an authorized technician.

The programmer determines the order in which to attempt family identification of an implantable cardiac device based on the information in the family histogram and the family identification times. The programmer first attempts to communicate with a given device using the communications protocols for the device families with the lowest predicted values of the expected time to be lost on average in unsuccessful identification attempts. Performing family identification in this order minimizes the total time consumed in identifying the family of the device.

Further features of the invention, its nature and various advantages will be more apparent from the accompanying drawings and the following detailed description of the preferred embodiments.

DETAILED DESCRIPTION OF THE PREFERRED EMBODIMENTS

Implantable cardiac devices such as pacemakers and cardioverter-defibrillators are presently available that apply electrical pulses to a patient's heart in order to maintain a healthy heart rhythm. Some implantable cardiac devices simply apply pacing pulses to the patient's heart at regular intervals. More typically, implantable cardiac devices contain sensing circuitry for monitoring the heartbeat signals produced by a patient's heart. Implantable cardiac devices with sensing circuitry can analyze the patient's heartbeat signals to determine when and at what energy level any electrical pulses should be applied to the heart.

To control the operation of an implantable cardiac device after it has been implanted in the patient's body, implantable cardiac devices are provided with numerous adjustable settings. For example, the energy at which pacing pulses are applied to patient's heart is usually an adjustable setting. Similarly, in a cardioverter-defibrillator a physician can adjust the shock energies of the defibrillation pulses. These device settings are adjusted by the physician using a device known as a programmer.

Programmers and implantable cardiac devices contain telemetry circuitry that allows a programmer and an implantable cardiac device to establish a wireless communications channel. The programmer can transmit commands to the implantable cardiac device over the channel to adjust the settings of the device. The device can transmit data to the programmer over the channel (e.g., for the programmer to analyze or display).

Figure 1:
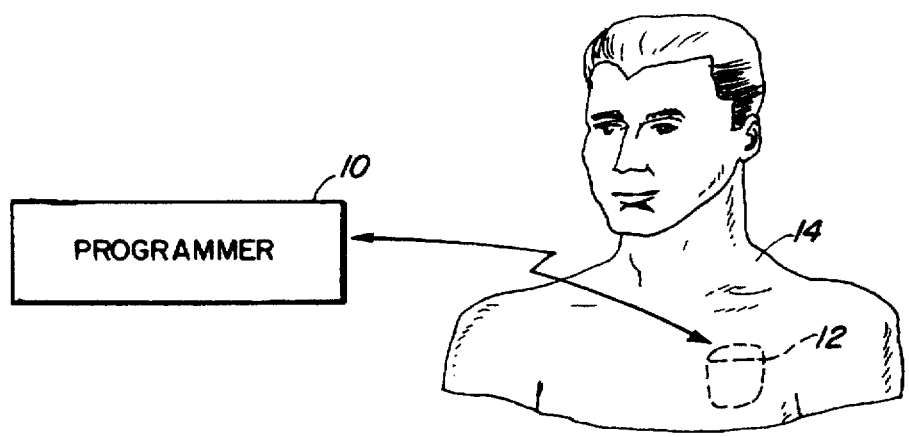
FIG. 1 is perspective view of a patient with an implantable cardiac device that is communicating with a programmer.

A typical arrangement is shown in FIG. 1. A physician uses a programmer 10 to adjust the settings of an implantable cardiac device 12 that has been implanted in the body of a patient 14. The programmer 10 and the implantable cardiac device 12 communicate telemetrically using a communications protocol (i.e., the various parameters associated with establishing a communications link between the programmer 10 and the implantable cardiac device 12, such as carrier frequency, bitrate, modulation technique, encoding scheme, etc.).

Different families of implantable cardiac devices use different communication protocols. For example, one family of implantable cardiac devices might use a bitrate of 8 kbps to communicate with the programmer 10, whereas another family of implantable cardiac devices might use a bitrate of 2 kbps. The programmer 10 cannot communicate with the implantable cardiac device 12 until a communications channel between the programmer 10 and the device 12 has been properly established. To establish such a channel, the programmer 10 must identify which family of device the implantable cardiac device 12 belongs to.

However, identifying an implantable cardiac device's family is a process of trial and error. This process can be cumbersome, because the programmer 10 does not have any information to indicate which communication protocols to try first in identifying the family. The programmer 10 proceeds systematically though the communications protocols for various device families, attempting to establish a communications channel between the programmer 10 and the implantable cardiac device 12 using each protocol. Each attempt to establish a communications channel and thereby identify the family of the device requires an identification time of about 0.5 to 2.0 seconds.

In the event that the physician needs to use the programmer to reset the device settings in an emergency situation (e.g., to place the device in a configuration providing maximum output pacing at a standard rate), being able to eliminate some of the time lost in making unsuccessful family identification attempts would be highly desirable.

Figure 2:
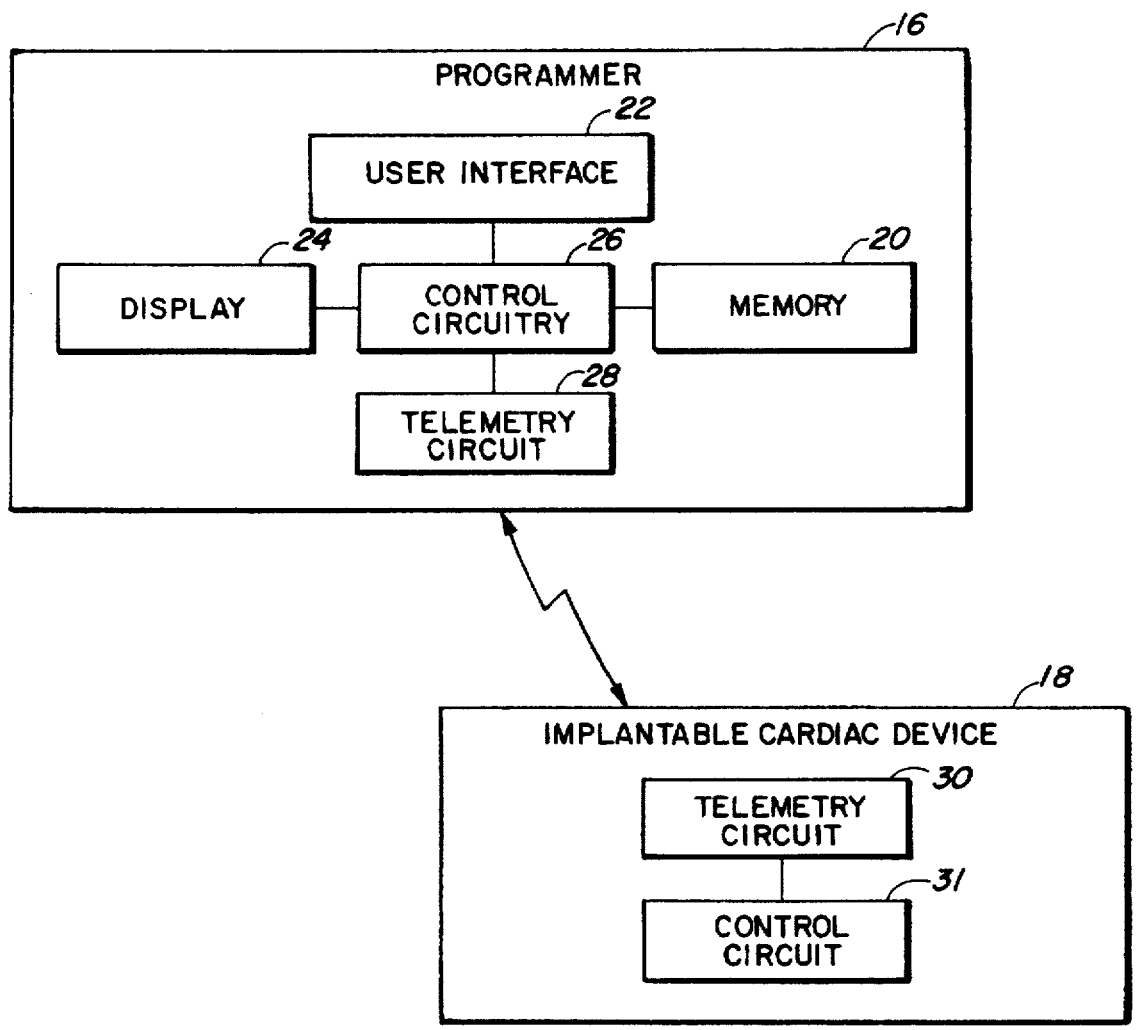
FIG. 2 is a schematic diagram of a programmer and an implantable cardiac device.

A programmer 16 and an implantable cardiac device 18 are shown in FIG. 2. In accordance with the present invention, the programmer 16 maintains in a memory 20 a record of which device families the programmer 16 has communicated. If desired, the record may be maintained in the form of a histogram. The memory 20 may be any suitable memory device, such as a hard disk drive or a battery-backed random-access memory. Also stored in the memory 20 are the identification times associated with identifying each family of implantable cardiac device 18. The family identification time information may be provided at the factory during the manufacture of the programmer 16 or may be provided in the field by an authorized technician.

The programmer 16 processes the histogram and family identification time information to determine the order in which each family's communication protocol should be used to attempt to communicate with the implantable cardiac device 18. Processing the histogram and family identification time information allows the programmer 16 to minimize the time it takes the programmer 16 to establish a communications channel with the implantable cardiac device 18.

A physician enters commands into the programmer 16 via user interface 22 (e.g., a keyboard or a touch screen). After a communications channel has been established with the implantable cardiac device 18, various data from the device 18 (such as cardiac data monitored by the device 18) can be presented on a display 24. Control circuitry 26 preferably contains dedicated control circuits and a microprocessor that executes instructions stored in the memory 20 to direct the overall operation of the programmer 16.

Telemetry circuitry 28 is used to communicate with telemetry circuitry 30 in the implantable cardiac device 18. The operation of the implantable cardiac device 18 is determined by control circuitry 32. The control circuitry 32 preferably contains dedicated control circuits and a microprocessor for executing instructions. In operation, additional circuitry in the implantable cardiac device 18 is used to provide pacing pulses, cardioversion/defibrillation shocks, etc.

Figure 3:
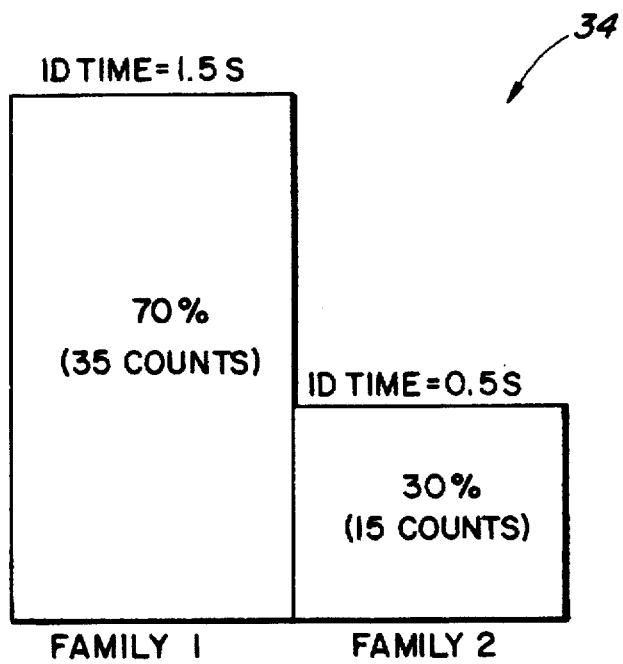
FIG. 3 is a implantable cardiac device histogram that is maintained by the programmer in accordance with the present invention.

The programmer 16 maintains a record (e.g., in the form of a histogram) of the various families of the implantable cardiac devices 18 that the programmer 16 has encountered. An illustrative histogram 34 is shown in FIG. 3. The histogram 34 indicates that the programmer 16 in which the histogram 34 is maintained has encountered two families of implantable cardiac device 18: family 1 and family 2. For example, family 1 might be the Affinity™ family of pacemakers of Pacesetter, Inc. of Sylmar, Calif. and family 2 might be the Pacesetter Microny™ family of pacemakers. The number of different families encountered by a given programmer may vary considerably, depending on the clinical environment in which the programmer 16 is used. Typically, more than two different families will be encountered, although two families are shown in FIG. 3 to avoid over-complicating the drawing.

The histogram 34 is preferably updated whenever the programmer 16 is successfully used by a physician to communicate with an implantable cardiac device 18. For example, a running count of each family type may be maintained in the memory 20 of the programmer 16. As shown in FIG. 3, 35 of the implantable cardiac devices 18 encountered by the programmer 16 maintaining the histogram 34 were in family 1 and 15 of the devices 18 were in family 2. The programmer 16 may determine an associated percentage or fractional value associated with these count values (i.e., 70% or 0.7 for family 1 and 30% or 0.3 for family 2).

If desired, the programmer 16 can attempt to identify a given implantable cardiac device 18 based on the count values for each family, e.g., by attempting to identify the devices 18 using the communications protocols suitable for the most popular families first, and then progressing to the less popular families. Such a technique may help eliminate some of the time that is now wasted in trying to identify the implantable cardiac devices 18 that are in families rarely encountered by the programmer 16. Preferably, however, the programmer 16 also uses information regarding the identification time required for each family to determine the order in which to attempt family identification.

Because each family of has a different communications protocol, the time necessary to establish a communications channel between the programmer 16 and the device 18 depends on the particular family of the device 18. For example, 1.5 seconds are required for the programmer 16 to successfully identify the devices 18 in family 1 and 0.5 seconds are required to identify the devices 18 in family 2. In situations such as the one in FIG. 3, the total time required to successfully identify the family of the implantable cardiac device 18 is minimized by first attempting to communicate with the device 18 in the less popular family (family 2).

The amount of time that is expected to be lost in unsuccessfully attempting to identify the family for the implantable cardiac device 18 (Lost_Time) is given by Equation 1.

$$\text{Lost\_Time} = (1-\text{Family\_Fraction}) * \text{ID\_Time} \quad (1)$$

Family_Fraction is the fractional population of a given family in the record of device encounters maintained by the programmer 16. For example, in the histogram 34, Family_ Fraction is 0.7 for family 1 and 0.3 for family 2. ID_Time is the estimated time required to identify an implantable cardiac device 18 as belonging to the family (i.e., the family identification time). The ID_Time for each family is dictated by the details of the communications protocol employed by that family of device 18 in communicating with the programmers 16. In the example of FIG. 3, the family identification time is 1.5 seconds for family 1 and 0.5 seconds for family 2.

In order to determine the order in which the communications protocols for the various families of devices should be used to attempt family identification, the programmer uses Equation 1 to predict the amount of time that it is expected will be lost on average in making unsuccessful attempts to establish a communications channel for each family. The quantity in brackets (1-Family_Fraction) represents the probability that the attempt will be unsuccessful. The second term in Equation 1 (ID_Time) is the amount of time that will be lost if the attempt is unsuccessful. Lost time predictions using Equation 1 for the example of FIG. 3 are given in Table 1.

TABLE 1

|          | Family_Fraction | ID_Time | Lost_Time |
|----------|-----------------|---------|-----------|
| Family 1 | 0.7             | 1.5 s   | 0.45 s    |
| Family 2 | 0.3             | 0.5 s   | 0.35 s    |

As shown in Table 1, it is expected that on average 0.45 seconds will be lost for each family identification attempt using the communications protocol suitable for establishing communications with family 1 implantable cardiac devices. It is expected that on average 0.35 seconds will be lost for each family identification attempt using the communications protocol suitable for establishing communications with family 2 implantable cardiac devices. Accordingly, the programmer 16 preferably attempts family identification using the communications protocol for family 2 before attempting family identification using the communications protocol for family 1. This approach minimizes the total time lost due to unsuccessful identification attempts and therefore makes the process of identifying the family of a given implantable cardiac device 18 more rapid.

Figure 4:
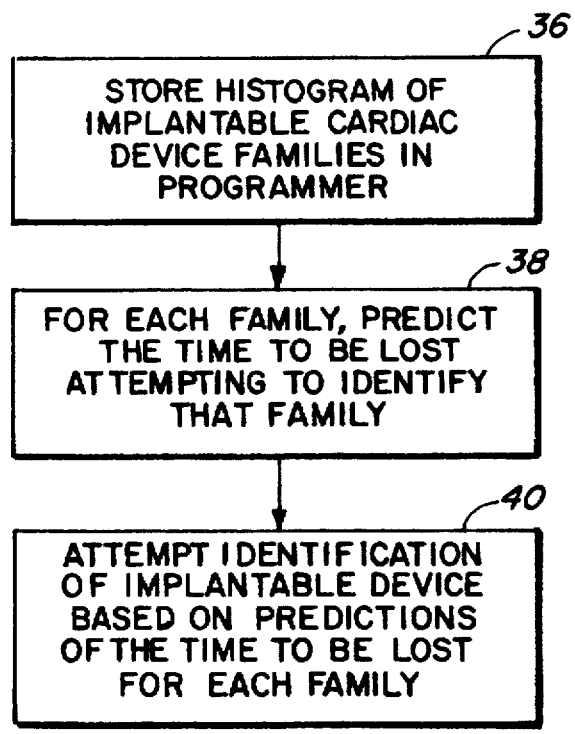
FIG. 4 is a flowchart of steps involved in the process of using the histogram of FIG. 3 to reduce the time spent identifying the family of an implantable cardiac device.

Steps involved in identifying the family of the implantable cardiac device 18 are shown in FIG. 4. At step 36, the programmer 16 updates the histogram (e.g., histogram 34 of FIG. 3) or other suitable record within the memory 20 with information regarding the most recent successful communication with an implantable cardiac device 18.

Updating the histogram to reflect recent communications ensures that the histogram data accurately reflects the probabilities of encountering similar devices in the future. The likelihood of encountering a device in a particular family in the future is assumed to be proportional to the frequency with which that family of device has been encountered by the programmer 16 in the past. The families that are encountered by a given programmer 16 reflect what types of the devices 18 the programmer 16 is being used to program.

The families commonly encountered by the programmer 16 vary depending on the type of market in which the programmer 16 is being used (e.g., the U.S. market versus the European market) and the type of clinical practice involved. In some situations, such as in specialty clinics, only certain types of devices 18 are encountered. For example, a clinic specializing in implantable cardioverter-defibrillators will rarely or never use the programmer 16 to communicate with a pacemaker. Because the histogram is automatically updated to reflect the fact that pacemakers are never encountered by that programmer, when the programmer 16 attempts family identification, it will use the communications protocols for implantable cardioverter-defibrillators, but not those of pacemakers. Avoiding the use of protocols that would probably be unsuccessful minimizes the time lost in unsuccessful identification attempts.

If desired, the histogram 34 can be updated using a weighted average, so that more recent encounters between the programmer 16 and the implantable cardiac devices 18 are given more weight than older encounters. In addition, the programmer 16 may be placed in a reset configuration (e.g., with a default or empty histogram) by an authorized field technician or by appropriate factory personnel.

At step 38 of FIG. 4, the programmer 16 predicts for each family the time that will be lost on average in unsuccessfully attempting to communicate with an implantable cardiac device 18 using the communications protocol for that family. This prediction is preferably made using Equation 1. At step 40, the programmer 16 attempts family identification of the implantable cardiac device 18 using communications protocols for the various families based on the lost time predictions made at step 38. Preferably, the programmer 16 first attempts family identification using the communications protocols for the families with the lowest predicted values of Lost_Time (Equation 1), thereby minimizing the total amount of time spent by the programmer 16 in identifying the family of the implantable cardiac device 18.

One skilled in the art will appreciate that the present invention can be practiced by other than the described embodiments, which are presented for the purposes of illustration and not of limitation, and the present invention is limited only by the claims that follow.

What is claimed is:

1. A method for using an implantable cardiac device programmer to identify which family of implantable cardiac device a given implantable cardiac device belongs to, comprising the steps of:

maintaining a record in the programmer of families of implantable cardiac device with which the programmer has successfully communicated; and identifying the family of the given implantable cardiac device with the programmer based on information contained in the record.

2. The method of claim 1, further comprising the steps of:

providing the programmer with a plurality of family identification times, the family identification time for each family representing the amount of time required to establish a communications channel between the programmer and implantable cardiac devices in that family; and making predictions of the expected time to be lost on average in unsuccessfully attempting to make a family identification for each of the families in the record based on the family identification times and information in the record, wherein the step of identifying the family of the given implantable cardiac device comprises the step of identifying the family of the given implantable cardiac device based on the predictions of the expected time to be lost.

3. The method of claim 2, wherein the step of maintaining the record comprises the step of updating a histogram in the programmer.

4. The method of claim 3, wherein the step of updating comprises the step of updating the histogram using a weighted average.

5. The method of claim 2, further comprising the step of using information in the record to determine a family fraction for each family, wherein the step of making predictions of the expected time to be lost comprises the step of determining a lost time value for each family by multiplying a first quantity equal to one minus the family fraction by a second quantity equal to the family identification time.

6. The method of claim 2, wherein the step of identifying the family comprises the step of identifying the family by first attempting to establish a communications channel between the programmer and the implantable cardiac device using communications protocols for families with the smallest values for the predictions of the expected time lost.

7. A system in which an implantable cardiac device programmer is used to identify which family of implantable cardiac device a given implantable cardiac device belongs to, comprising:

means for maintaining a record in the programmer of families of implantable cardiac device with which the programmer has successfully communicated; and means for identifying the family of the given implantable cardiac device with the programmer based on information contained in the record.

8. The system of claim 7, further comprising:

means for providing the programmer with a plurality of family identification times, the family identification time for each family representing the amount of time required to establish a communications channel between the programmer and implantable cardiac devices in that family; and means for making predictions of the expected time to be lost on average in unsuccessfully attempting to make a family identification for each of the families in the record based on the family identification times and information in the record, wherein the means for identifying the family of the given implantable cardiac device comprises means for identifying the family of the given implantable cardiac device based on the predictions of the expected time to be lost.

9. The system of claim 8, wherein the means for maintaining the record comprises means for updating a histogram in the programmer.

10. The system of 9, wherein the means for updating comprises means for updating the histogram using a weighted average.

11. The system of claim 8, further comprising means for using information in the record to determine a family fraction for each family, wherein the means for making predictions of the expected time to be lost comprises means for determining a lost time value for each family by multiplying a first quantity equal to one minus the family fraction by a second quantity equal to the family identification time.

12. The system of claim 8, wherein the means for identifying the family comprises means for identifying the family by first attempting to establish a communications channel between the programmer and the implantable cardiac device using communications protocols for families with the smallest values for the predictions of the expected time lost.

* * * * *